United States Patent [19]

Kroll

[11] Patent Number: 5,713,944
[45] Date of Patent: Feb. 3, 1998

[54] CARDIOVERSION-DEFIBRILLATION CATHETER LEAD HAVING SELECTIVELY EXPOSABLE OUTER CONDUCTORS

[75] Inventor: Mark W. Kroll, Minnetonka, Minn.

[73] Assignee: Angeion Corporation, Plymouth, Minn.

[21] Appl. No.: 600,749

[22] Filed: Feb. 13, 1996

[51] Int. Cl.$^6$ .................................. A61N 1/05; A61N 1/04
[52] U.S. Cl. .................................................. 607/122
[58] Field of Search .................................. 607/122, 123, 607/125, 126

[56] References Cited

U.S. PATENT DOCUMENTS

| | | | |
|---|---|---|---|
| 5,016,646 | 5/1991 | Gotthardt et al. | 607/122 |
| 5,111,830 | 5/1992 | Bemurat | 607/122 |
| 5,235,978 | 8/1993 | Hirschberg et al. | |
| 5,246,014 | 9/1993 | Williams et al. | |
| 5,263,977 | 11/1993 | Adams et al. | 607/122 |
| 5,265,623 | 11/1993 | Kroll et al. | |
| 5,269,319 | 12/1993 | Schulte et al. | 607/123 |
| 5,325,870 | 7/1994 | Kroll et al. | |
| 5,405,363 | 4/1995 | Kroll et al. | |
| 5,454,839 | 10/1995 | Andrsonet et al. | |
| 5,476,496 | 12/1995 | Strandberg et al. | |
| 5,478,493 | 12/1995 | Muff. | |
| 5,578,067 | 11/1996 | Ekwall et al. | 607/122 |

Primary Examiner—Marvin M. Lateef
Assistant Examiner—Carl H. Layno
Attorney, Agent, or Firm—Brad Pedersen

[57] ABSTRACT

A cardioversion/defibrillation catheter lead has selectively exposable outer conductors that increase the effective electrode area and that can be used to direct electrical countershock vectors delivered by the catheter lead. The lead includes an elongated catheter body having a proximal end, a distal end and a catheter length. The catheter body includes at least one electrical conductor surrounded by a dielectric tubular sheath and an outermost dielectric tubular sheath. Each electrical conductor is electrically connected to an electrical connector located at the proximal end of the catheter body and to a cardioversion/defibrillation electrode located long the catheter body between the proximal end and the distal end. At least a portion of the outermost dielectric tubular sheath includes structure for selectively removing that portion of the outermost tubular sheath, thereby creating an effective length of at least one of the electrodes which is longer than an original length of that electrode. The selectively removable portion of the catheter lead allows that portion of the catheter body to be utilized as an additional electrode, and also allows for the length and relative distance between a first and second electrode along the catheter body to be optimized for the particular dimensions of a patient.

12 Claims, 8 Drawing Sheets

CARDIOVERSION-DEFIBRILLATION CATHETER LEAD HAVING SELECTIVELY EXPOSABLE OUTER CONDUCTORS

FIELD OF THE INVENTION

The present invention relates to catheter lead systems for implantable cardioversion/defibrillation systems and, in particular, the present invention relates to a cardioversion/defibrillation catheter lead having selectively exposable outer conductors that increase effective electrode areas and can be used to direct electrical countershock vectors delivered via these lead systems.

BACKGROUND OF THE INVENTION

The use of implantable cardioverter defibrillator (ICD) systems as a medical therapy for persons with abnormal heart conditions, or arrhythmias, is well known. It is also well known to use implantable catheter leads for carrying the defibrillation electrodes necessary to deliver a cardioversion/defibrillation countershock from the ICD system. Examples of such cardioversion/defibrillation catheter leads are shown in U.S. Pat. Nos. 5,265,623 and 5,454,839. In all of the existing cardioversion/defibrillation catheter leads, the size of the cardioversion/defibrillation electrodes carried on the catheter lead is fixed. Typically, a first cardioversion/defibrillation electrode is between 5 and 10 centimeters in length, is located at a distal end of the catheter lead for insertion into the right ventricle (RV). In some embodiments, a second cardioversion/defibrillation electrode of a length from 2.5 to 7.5 centimeters is positioned along the catheter lead toward the proximal end, a distance from the first electrode so as to proximately position this second electrode within the superior vena cava (SVC). A further length of catheter lead surrounded by insulative material, typically silicon, extends from the proximal end of either the first or second electrode to an electrical connector at the proximal end of the catheter lead. The electrical connector is adapted to be connected to a header block of the ICD system.

Although existing catheter leads have proven useful in simplifying the implantation procedures for ICD systems, the cardioversion/defibrillation electrodes carried on these catheter lead systems typically offer less total electrode surface area than conventional ICD electrodes, such as epicardial or subcutaneous patch electrodes. In addition, due to the fixed lengths of the cardioversion/defibrillation electrodes, and their fixed relationship to each other in those embodiments of the catheter lead having two electrodes, it is necessary for a physician to maintain a plurality of different sizes of the catheter leads in order to optimize the fixed positioning of the electrodes to a particular patient in which the catheter lead will be implanted. Accordingly, it would be desirable to provide a cardioversion/defibrillation catheter lead which could retain the implantation advantages of a catheter lead, while reducing the disadvantages of conventional catheter leads.

SUMMARY OF THE INVENTION

The present invention is a cardioversion/defibrillation catheter lead having selectively exposable outer conductors that increase the effective electrode area and that can be used to direct electrical countershock vectors delivered by the catheter lead. The lead includes an elongated catheter body having a proximal end, a distal end and a catheter length. The catheter body includes at least one electrical conductor surrounded by a dielectric tubular sheath and an outermost dielectric tubular sheath. Each electrical conductor is electrically connected to an electrical connector located at the proximal end of the catheter body and to a cardioversion/defibrillation electrode located along the catheter body between the proximal end and the distal end. At least a portion of the outermost dielectric tubular sheath includes a structure for selectively removing that portion of the outermost tubular sheath, thereby creating an effective exposed length of at least one of the electrodes which is longer than an original length of that electrode. The selectively removable portion of the catheter lead allows that portion of the catheter body between the proximal end of the electrodes and the electrical connector to be utilized as an additional electrode and also allows for the length and relative distance between a first and second electrode along the catheter body to be optimized for the particular dimensions of a patient.

In a preferred embodiment, the selectively removable outermost tubular dielectric sheath is comprised of manually and selectably removable sections. These manually removable sections may be defined by perforations generally longitudinally and circumferentially about the catheter body. The manually removable sections may also be defined by embedded filaments, the filaments extending generally longitudinally and circumferentially about the catheter body. Alternatively, the manually removable sections may be defined by perforations and filaments, both generally longitudinally and circumferentially disposed about the catheter body.

DETAILED DESCRIPTION OF THE DRAWINGS

Comprehension of the present invention can be gained through reference to the drawings in conjunction with a thorough review of the following explanation.

Figure 1:
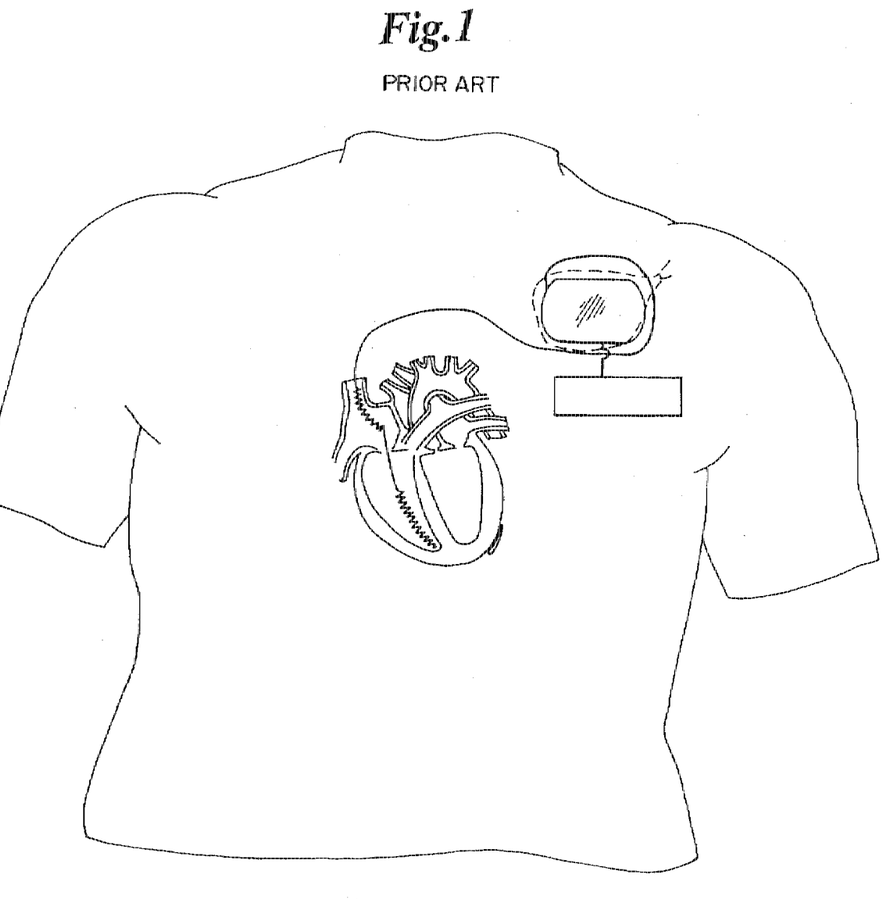
FIG. 1 depicts a prior art ICD electrode system.

FIG. 1 depicts a prior art ICD electrode system with two endocardial cardioversion-defibrillation lead electrodes disposed within the heart. The pulse generator contains batteries and circuitry for generating a series of countershocks and sensing circuitry for detecting an arrhythmic event. Such pulse generator is taught in U.S. Pat. Nos. 5,405,363 and 5,447,521 and detection of fibrillation and tachycardia are taught in U.S. Pat. No. 5,366,487, the entire disclosures of which are hereby incorporated by reference. The exterior of the pulse generator may serve as an electrode surface. The lead is connected to the pulse generator and terminates with two cardioversion/defibrillation electrodes. The distalmost RV electrode is located within the right ventricle, its distal tip proximate to the right ventricular apex. The more proximal RA/SVC electrode is situated within the right atrium and/or superior vena cava. Though not shown, a sole single electrode located within the right ventricle could be employed.

The box connected to the pulse generator may be either a subcutaneous patch, a "pitchfork" electrode or other electrode surface implanted exterior to the thoracic cavity. An epicardial patch electrode is also depicted. In contrast to the other subcutaneously implanted electrodes, emplacement of an epicardial patch is the most invasive and, therefore, riskiest procedure, since the thoracic cavity must be opened. Though not shown, other electrode surfaces can be implanted within the coronary sinus/great vein and the inferior vena cava. The purpose of these electrode surfaces exterior to the heart is to provide one or more electrodes of opposite polarity to at least one of the electrodes implanted within the heart, itself, enabling an electrical countershock vector to travel through fibrillating ventricular tissues.

If the countershock vector is directed through a sufficient amount of the defibrillating ventricular heart tissue and if the wave form of the countershock is adequate in form and in amplitude, fibrillation will cease and the heart will resume normal contractions.

Figure 2:
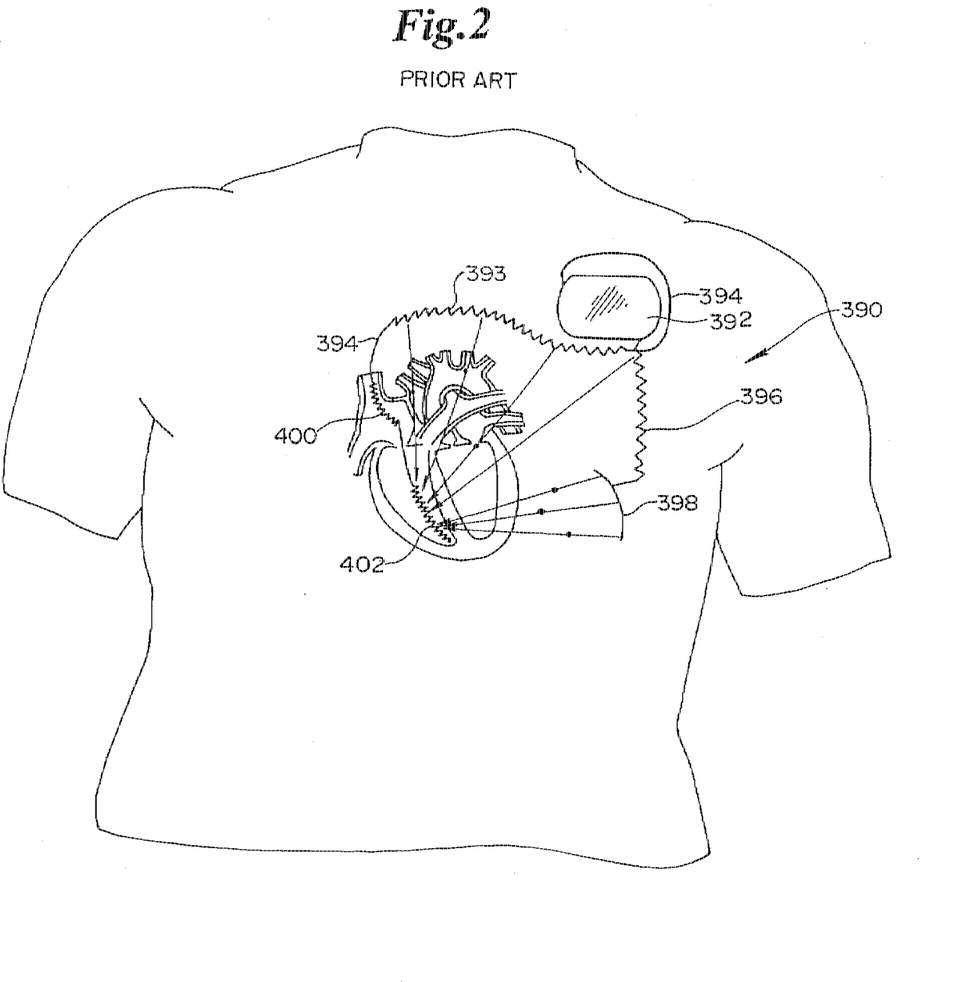
FIG. 2 depicts an ICD electrode system in accordance with the present invention.

FIG. 2 shows an ICD electrode system of the present invention wherein a lead with an exposed outer conductor is used as an electrode surface in combination with a subcutaneous patch and two endocardial lead electrodes. ICD system 390 has pulse generator 392 in electrical communication with insulated lead 394. Pulse generator 392 may be of the design previously discussed and incorporated by reference with respect to FIG. 1. Insulated lead 394 has a portion of its outer insulation selectively removed, thereby exposing outer conductive lead surface 393. Distally on lead 394 are disposed SVC/RA electrode 400 and RV electrode 402. Subcutaneous patch 398 is electrically connected to pulse generator 392 by cable 396.

The increase in electrode surface area of ICD system 390 represents a considerable advance over that of the prior art. By selectively removing portions of outer insulated areas, electrical countershock vectors can be more accurately directed to include critical portions of the heart. As also shown in FIG. 2, the electrical current vectors are depicted as emanating from subcutaneous patch 398 and from the portion of lead 394 with an exposed outer conductor 393, traveling to RV electrode 402. Another current vector is depicted as originating from SVC/RA electrode 400 traveling through portions of the right atrium and right ventricle to RV electrode 402. Here as in other embodiments of the present invention, polarities of any or all of the electrode surfaces could be reversed, thereby reversing the direction of travel of associated countershock vectors.

Although a subcutaneous patch electrode and its connecting cable are depicted, other electrode surfaces, such as a "pitchfork" electrode or electrodes disposed within the coronary sinus/great vein or the inferior vena cava may be employed as desired. Finally, the subcutaneous patch electrode and its connecting cable, as well as all other nonlead electrodes, may be totally eliminated from the ICD system of the present invention if the exposed outer conductor 393, and perhaps the presence of an active electrode surface on pulse generator 392 (not shown), is sufficient to enable a defibrillating countershock vector to depolarize enough ventricular tissue to restore normal heartbeat.

Figure 3:
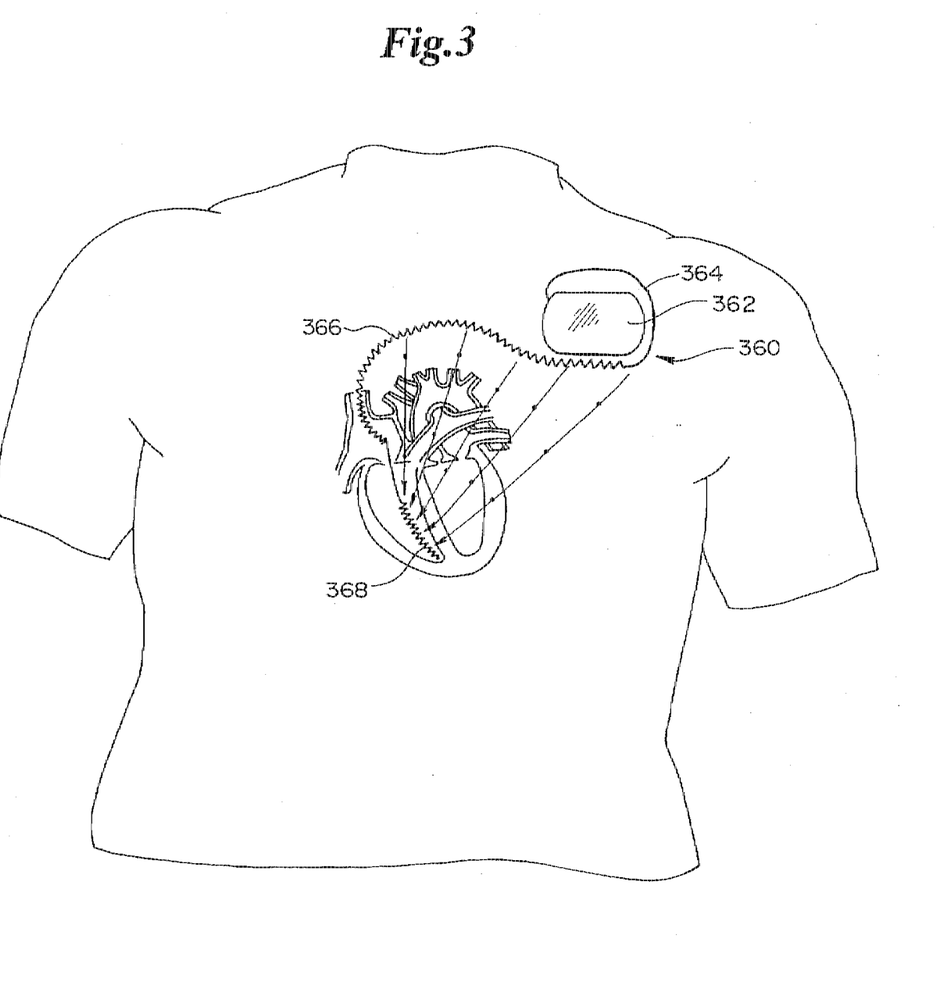
FIG. 3 depicts an alternative embodiment of an ICD electrode system in accordance with the present invention.

In FIG. 3 is shown an ICD electrode system of the present invention wherein a lead with an exposed outer conductor extends from the right atrium/superior vena cava region proximally toward the pulse generator. This extended electrode/exposed outer conductive surface is utilized as a cardioversion/defibrillation electrode in combination with a distal electrode disposed in the right ventricle. ICD system 360 has pulse generator 362 and insulated lead 364. Pulse generator 362 may be of the type discussed and incorporated by reference with respect to FIG. 1. Distal from its connection point to pulse generator 362 is a removable outer insulation on insulated lead 364. This portion of lead 364 having a removable outer insulation extends from a point distal to the point of attachment of lead 364 to pulse generator 362 to a point well within the right atrium of the heart. Some or all of the removable outer insulation can be selectively removed, thereby exposing a potentially continuous outer conductive electrode surface 366.

As shown in FIG. 3, a current vector extends from the continuous exposed outer conductive surface 366 of lead 364 to RV electrode 368 disposed within the right ventricle and proximate to the right ventricular apex. Even with only two active electrode surfaces, the area of the heart which can be encompassed by the electrical vector is considerable. As in all other embodiments, the polarities of the two electrode surfaces of this embodiment can be reversed, thereby reversing the direction of the electrical countershock vector. The addition of an active pulse generator exterior as an electrode surface to ICD system 360 would further enhance the available electrode surface area without the need to separately implant other electrode surfaces.

If desired, other electrode surfaces not shown may be employed with this embodiment of the present invention. These include a subcutaneous patch and a "pitchfork" electrode. Also included might be electrodes implanted within the coronary sinus/great vein and the inferior vena cava. Less desirably, an epicardial patch could also be used.

Figure 4:
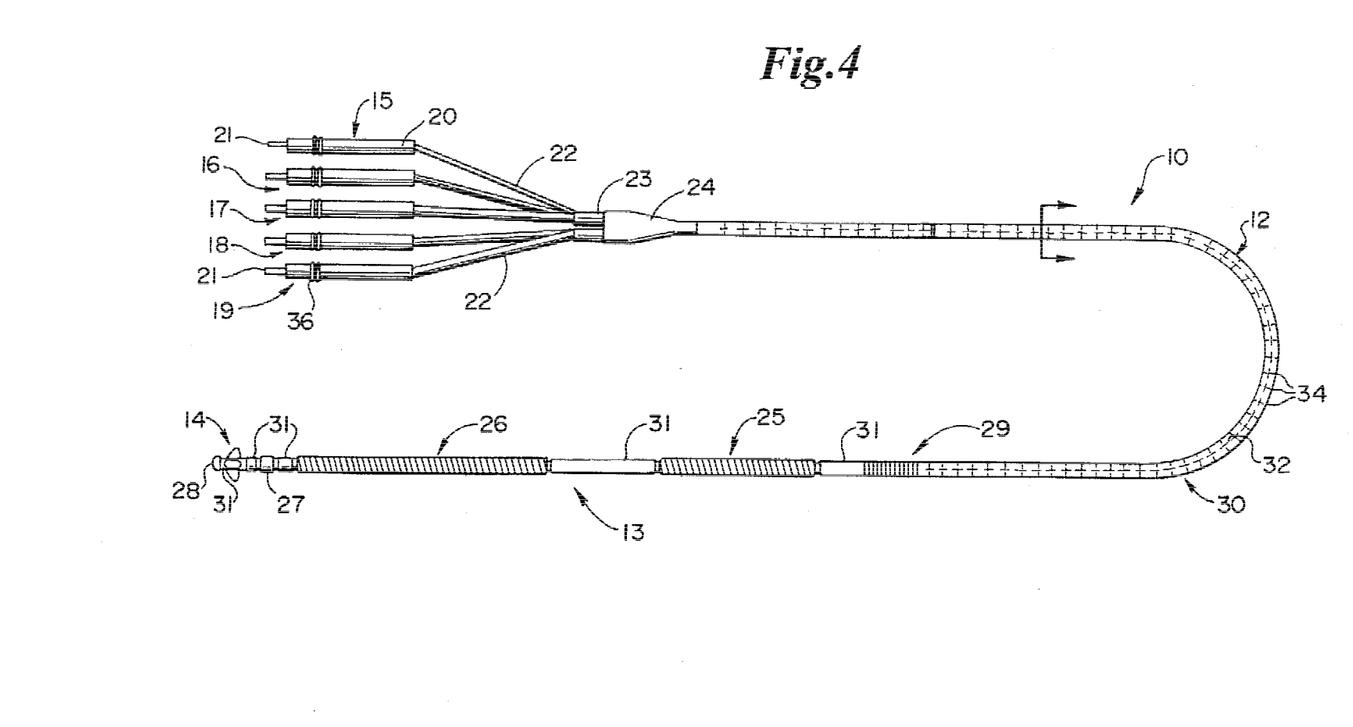
FIG. 4 depicts an ICD catheter lead in accordance with the present invention.
Figure 5:
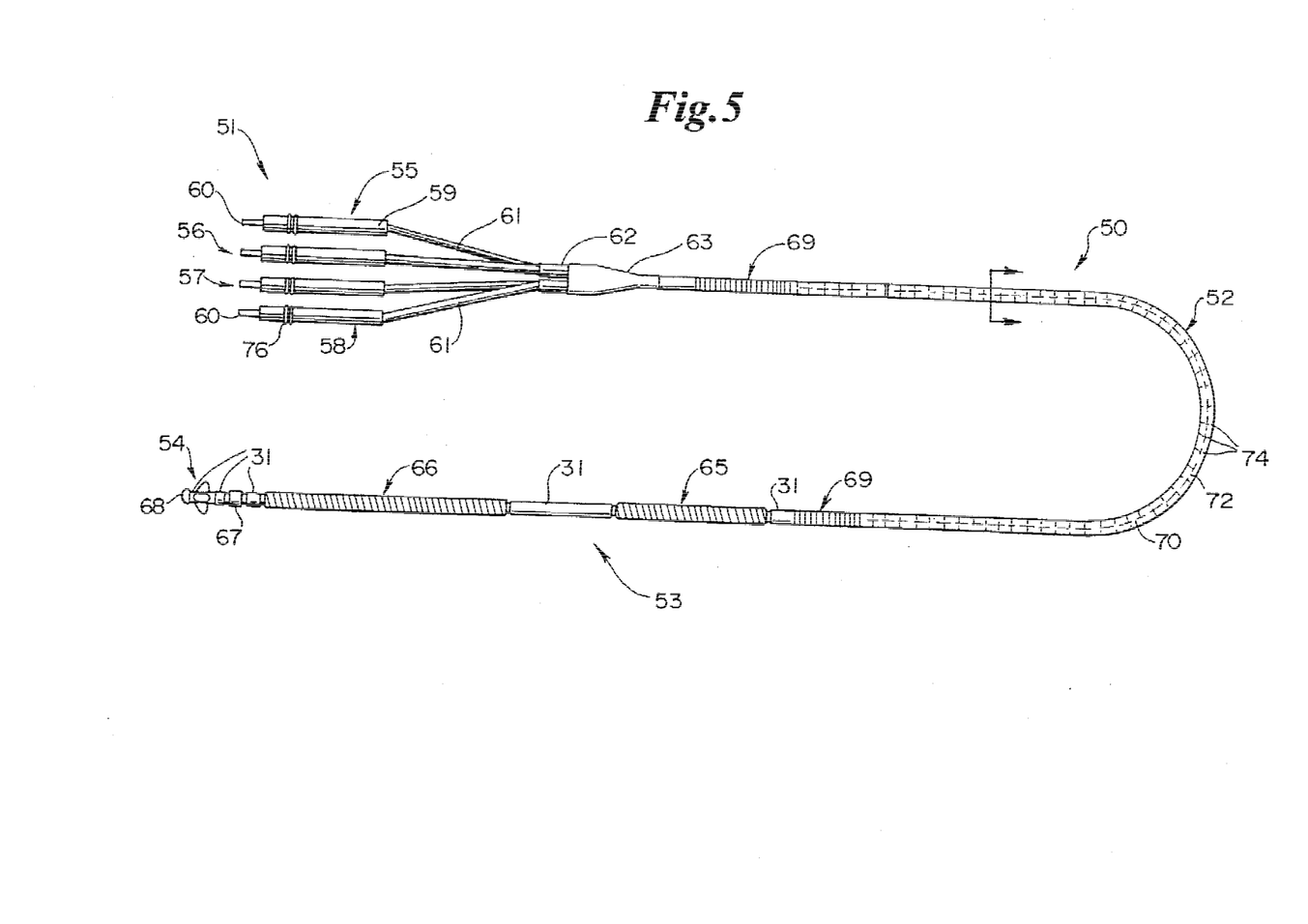
FIG. 5 depicts an alternate embodiment of an ICD catheter lead in accordance with the present invention.
Figure 6:
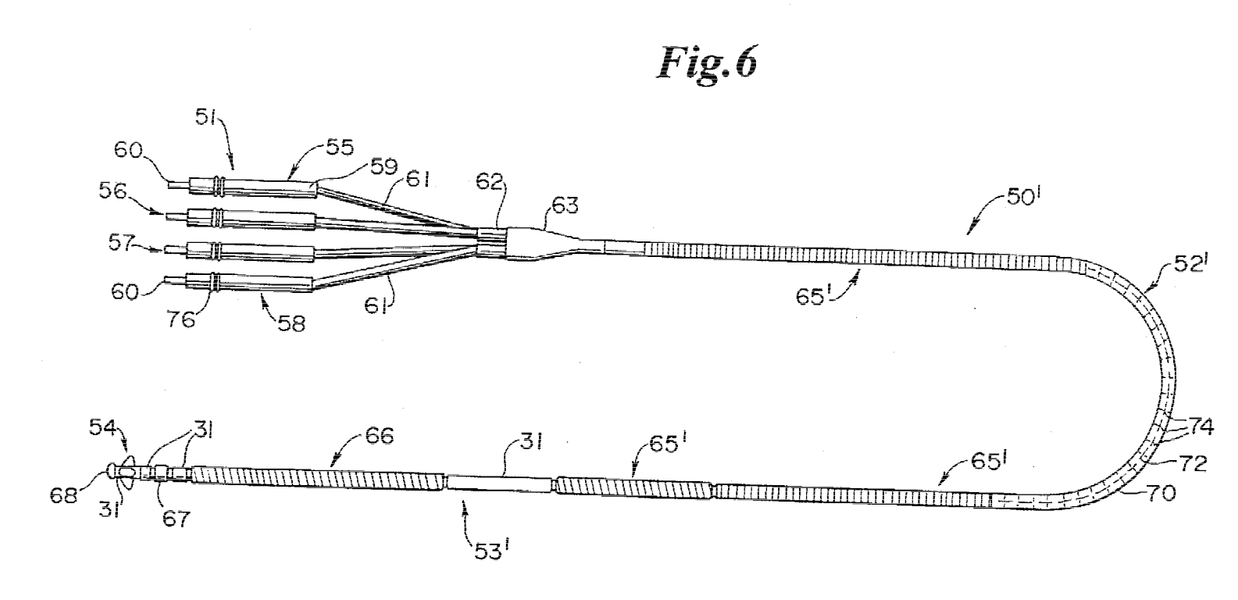
FIG. 6 depicts another alternative embodiment of an ICD catheter lead in accordance with the present invention.

FIG. 4 depicts an ICD lead of the present invention with two cardioversion/defibrillation electrodes, two pacing/sensing electrodes and a cable with a removable outer insulation covering an outer conductor utilized as an electrode when exposed. This embodiment, as well as those of FIGS. 5 and 6, is also described generally in U.S. Pat. No. 5,265,623, the entire contents of which are hereby incorporated by reference. In this embodiment lead 10 has a connection end 11, a cable 12, and an electrode end 13.

Connection end 11, in turn, has a series of terminal lead connectors 15-19. Each terminal lead 15-19 is composed of a lead plug 20 having an end tip 21 at its proximal end. End tip 21 on each terminal lead is embedded within lead plug 20. Lead plug 20 is comprised of a dielectric material. Sealing rings 36 are disposed on the exterior of each lead plug 20 to hermetically seal the connection from body fluids when the lead plugs are connected to pulse generator ports. Distal to lead plugs 20 are insulated lead conductors 22 for each terminal lead. The insulated lead conductors 22 are gathered distally in strain relief sheath 23. Distal to strain relief sheath 23 is lead collector 24.

The exterior of cable 12 is removable outer insulation 30. Removable outer insulation 30 is perforated generally longitudinally and circumferentially. Longitudinal perforation 32 preferably extends the length of removable outer insulation 30. At distances approximately one centimeter apart are contained circumferential perforations 34. Circumferential perforations 34 and longitudinal perforation 32 thereby define manually removable sections of selectively removable outer insulation 30. In this embodiment there may be more than one longitudinal perforation 32. If more than one longitudinal perforation 32 is present, optimally the longitudinal perforations 32 will be disposed oppositely on removable outer insulation 30. In FIG. 4 is depicted an area where a portion of outer removable insulation 30 has been removed, exposing outer conductor 29.

Electrode end 13 lies distal to and separated from cable 12 by a length of removable outer insulation 31. Distal to the area wherein the outer conductor 29 is exposed lies proximal cardioversion/defibrillation electrode 25. Distal to electrode 25 is another area of outer nonremovable outer insulation 31. Distal to this area of outer insulation 31 is distal cardioversion/defibrillation electrode 26. Distal to and separated from electrode 26 by another nonremovable length of outer insulation 31 is proximal pace/sense electrode 27. Distal to electrode 27 is anchor structure 14. Anchor structure 14 is flanked by nonremovable lengths of outer insulation 31. Distal to anchor structure 14 and on the distal terminus of lead 10 is distal pace/sense electrode 28.

In this embodiment terminal leads 15, 16, 17 and 18 are in electrical communication with electrodes 25, 26, 27 and 28, respectively, via conductors within cable 12 and discussed below. Terminal lead 19 is in electrical communication with outer conductor 29. Any electrode surface of the present invention may be constructed from materials such as plathinum-iridium wire, MP35N™ wire, silver core MP35N™ wire, or noble metal coated MP35N™ wire (with or without a silver core). MP35N™ is an alloy comprising nickel, cobalt, chromium and molybdenum and is manufactured by Maryland Specialty Wire Company of Cockeysville, Md. Removable outer insulation 30 of lead 10 may be manufactured from implantable grade silicon rubber, polytetrafluoroethylene resin (Teflon®) or polyurethane or any other dielectric material suitable for the purpose as known in the art.

In FIG. 5 is depicted an ICD electrode system of the present invention with two cardioversion/defibrillation electrodes, two pacing/sensing electrodes and a cable with a removable outer insulation covering an outer conductor utilized as an electrode when exposed and connected to the active electrode housing surface of a pulse generator. Lead 50 has connection end cable 52 and electrode end Connection end 51, in this embodiment, has four terminal leads 55, 57 and 58. As in the embodiment of FIG. 4, each terminal lead, at its proximal end, has a plug end tip 60. Each terminal lead is further comprised of a lead plug end 59 also comprised of a dielectric material. Disposed on the exterior of each terminal lead are two sealing rings 76. Sealing rings 76 serve to hermetically seal the lead connection from body fluids when connected to a pulse generator. Distal to lead plug end 59 are insulated lead conductors 61. Insulated lead conductors 61 are collected within strain relief sheath 62. Proximal and adjacent to strain relief sheath 62 is lead collector 63.

Cable 52, as in the embodiment of FIG. 4, is completely covered by removable outer insulation 70. Removable outer insulation 70 is perforated longitudinally and circumferentially. Longitudinal perforation 72 optimally extends the entire length of removable outer insulation 70. If desired, another longitudinal perforation 72 may be disposed, preferably opposite longitudinal perforation depicted in this embodiment. A series of circumferential perforations 74 is depicted as being approximately one centimeter apart, although other spacing dimensions for circumferential perforations 74 are well within the spirit and scope of the present invention. As removable outer insulation 70 is selectively removed, a portion of outer conductor 69 is exposed.

Electrode end 53 of cable 52 has at its proximal end, proximal cardioversion/defibrillation electrode 65. Proximal and distal to electrode 65 are lengths of nonremovable outer insulation 31. Distal to this length of outer insulation 31 is distal cardioversion/defibrillation electrode 66. Distal to electrode 66, and separated by another length of nonremovable outer insulation 31, is proximal pace/sense electrode 67. Distal to electrode 67 is anchor structure 54, which is also flanked by sections of nonremovable outer insulation 31. Distal to anchor structure 54 is distal pace/sense electrode 68. Insulation and conductive/electrode portions of the embodiment of FIG. 5 may be constructed of the same materials as described with respect to FIG. 4. In the embodiment of FIG. 5, a fifth terminal lead as depicted in the embodiment of FIG. 4 and in electrical communication with outer conductor 29 of FIG. 4 is not present. Therefore in this embodiment of the present invention, outer conductor 69 may be connected to the active exterior of a pulse generator, as described below. Terminal leads 55, 56, 57 and 58 are in electrical communication with electrodes 65, 66, 67 and 68, respectively, via conductors within cable 52.

FIG. 6 depicts an ICD electrode system of the present invention with a RV cardioversion/defibrillation electrode, two pacing/sensing electrodes and a continuous outer conductor beginning at the RA/SVC position and proceeding proximally the length of the lead cable. Lead 50' has connection end 51, cable 52' and electrode end 53'. Connection end 51 is configured as described with respect to the corresponding structure in FIG. 5. Cable 52' of lead 50' has a removable outer insulation 70. Removable outer insulation 70, as in previous embodiments, has a longitudinal perforation 72 extending the length of removable outer insulation 70. Disposed at approximately one centimeter intervals are circumferential perforations 74. As in previous embodiments, an additional longitudinal perforation 72 may be present, preferably opposite the longitudinal perforation depicted and circumferential perforations 74 may be spaced differently than one centimeter.

Removable outer insulation 70 may be removed partially or in its entirety to expose all or parts of outer conductor 65'. Outer conductor 65' extends from a point distal to lead collector 63 to a location of lead 50' which would normally be disposed well within either the right atrium or superior vena cava of the patient's heart.

Distal to exposed outer conductor 65' and separated from it by a length of nonremovable outer insulative material 31 is distal cardioversion/defibrillation electrode 66. Distal to electrode 66 is another length of nonremovable outer insulative material 31. Separating electrodes 67 and 68 is anchor structure 54, flanked by two lengths of nonremovable insulative materials 31.

In the embodiment of FIG. 6, selectively removing all or portions of removable outer insulation 70 can alter the amount of effective electrode surface on lead 50' as well as directing the resulting electrical countershock vector between an active housing exterior/exposed outer conductor 65' and electrode 66. The inclusion of other electrode surfaces, such as a "kite tail" or a subcutaneous patch would further enable varying vectors at many desirable locations as well as enabling countershock vectors of sufficiently high energy to effect defibrillation. In this embodiment, terminal leads 55, 56, 57 and 58 are in electrical communication with exposed outer conductor 65', and electrodes 66, 67 and 68, respectively, via conductors within cable 52'. Conductive and dielectric elements may be made from the materials as discussed with respect to FIG. 4.

As is known in the art, the function of the electrodes of FIGS. 4-6 may be varied, depending upon the particular ICD apparatus utilized in the medical application, by altering the connection scheme of the leads therein. When required, one or more of the electrodes may be rendered inoperative. Finally, the catheters of these figures can be reconfigured, consistent with the teachings of this invention to have two or three electrodes to suit particular medical applications.

The spacing of the electrodes of FIGS. 4-6 is a function of the structure and dimensions of the human heart and of the prescribed location of the electrodes therein, typically at the junction of the superior vena cava to the heart and within the left ventricle. Additionally, the length and outer surface of the electrodes is selected to maximize current distribution to the patient's heart tissue. The diameters of the cylindrical electrodes are preferably between 6-9 French and, more preferably, 6 French, or less.

Figure 7:
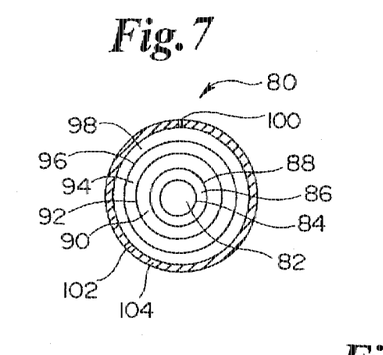
FIG. 7 depicts a cross section of a concentric five conductor cable of the present invention as depicted in FIGS. 4, 5 and 6.

FIG. 7 depicts a cross-section of a concentric five conductor cable of the present invention as depicted in FIGS. 4-6. Lumen 82 is disposed in the center of cable 80. During implantation, a stylet (not depicted) may be inserted within lumen 82 to guide the lead of the present invention as the lead is passed intravenously through the vascular system into the heart. Once inside the heart, the styler is further used to effect placement at the desired location and to implant the anchor structure proximate to the apex of the right ventricle. Once the lead is emplaced at the desired location, the stylet is withdrawn. Exterior to lumen 82 is first conductor 84. Concentric and exterior to first conductor 84 are second conductor 88, third conductor 92 and fourth conductor 96, respectively. Between first conductor 84, second conductor 88, third conductor 92 and fourth conductor 96 are layers of a dielectric insulative material as depicted by elements 86, 90 and 94, respectively. Exterior to fourth conductor 96 is another layer of dielectric insulative material 98. Exterior to insulative layer 98 is outer conductor 102. Surrounding outer conductor 102 is removable outer insulation 104. Longitudinal perforation 100 is depicted as disposed within removable outer insulation 104 and will be discussed below. The insulative and conductive materials of FIG. 7 are the same as those depicted for the catheter as a whole and as described with respect to FIG. 4. Though not depicted, alternate conductor and insulator arrangements as known in the art are well within the scope and spirit of the present invention, such as multi-lumen insulation.

Figure 8:
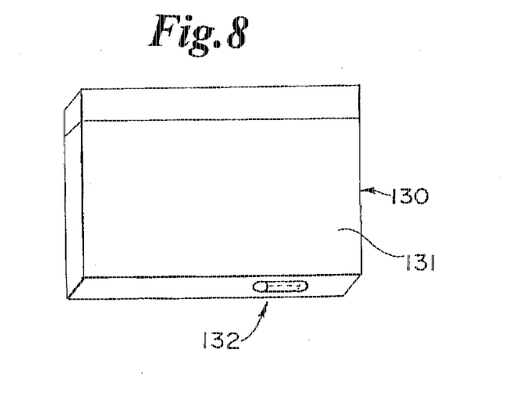
FIG. 8 depicts a pulse generator with a housing exterior used as an electrode and a cylindrical tube used to electrically connect an exposed outer conductor of the present invention to the housing exterior.

FIG. 8 depicts a pulse generator of the present invention with a housing exterior, which may be used as an active electrode surface, and a cylindrical tube used to electrically connect the exposed outer conductor of the present invention to the housing exterior. A pulse generator with an active electrode surface was discussed and incorporated by reference with respect to FIG. 1. Closable cylinder 132 is attached to active surface 131 of pulse generator 130. Cylinder 132 may be attached to surface 131 by riveting, resistance welding, laser welding or any method known in the art. Other mechanisms for effecting a mechanical and electrical connection of exterior 131 with the exposed outer conductors of the present invention are well within the spirit and scope of this invention.

Figures 9, 10:
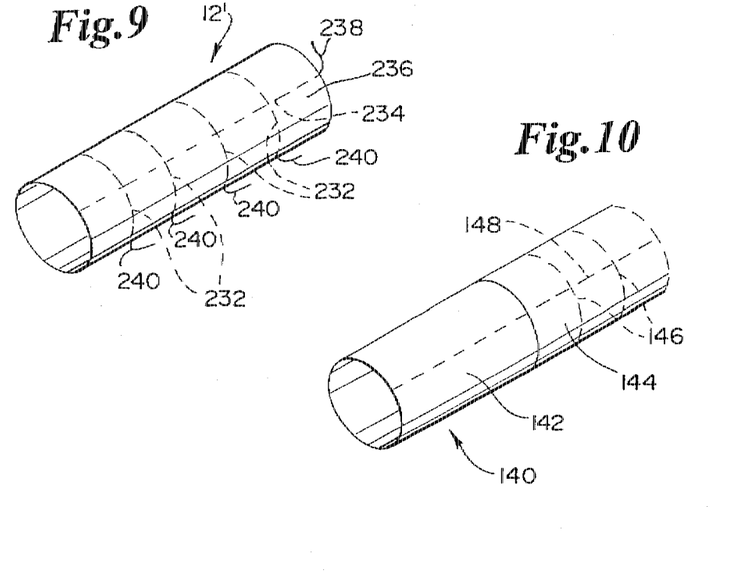
FIG. 9 depicts an embodiment of the outer removable insulation of the present invention with generally circumferential and longitudinal perforations and with filar wires embedded within the perforations.
FIG. 10 depicts an embodiment of the outer conductive surface of the present invention.

In FIG. 9 is depicted the outer removable insulation of the present invention with circumferential and longitudinal perforations and with filar wires embedded within the perforations. Cable 12' has as its exterior a removable outer insulation 236. Within removable outer insulation 236 are deployed one or more longitudinal perforations 234 and circumferential perforations 232, as previously described. Embedded within longitudinal perforation 234 and circumferential perforations 232 are filaments 238 and 240, respectively. Filaments 238 and 240 can be either a filar wire or other materials such as nylon or cotton filaments.

To remove the desired defined sections of removable outer insulation 236, embedded filaments 238 and 240 can be pulled either with the fingers, surgical forceps, or any other instrument until the desired lengths are pulled away from and out of outer insulation 236 thereby severing the desired portion. When the desired portion is thereby severed, the remaining severed sections of outer insulation 236 can be removed from cable 12', exposing the selected portion of the outer conductor. Extruding circumferential filaments 238 and 240 are severed at the surface of removable outer insulation 236 when removal of their corresponding sections is not desired. Though shown as including both filaments and perforations, the removable sections of the present embodiment can be defined by either alone and still be within the spirit and scope of this invention.

In FIG. 10 is depicted an embodiment of the outer conductive surface of the present invention wherein the outer conductor is a continuous, smooth surface layer of conductive material. The exterior of cable 140 is a removable outer insulation 144. One or more longitudinal perforations 148 and circumferential perforations 146 as previously described may be present. A continuous outer conductive layer 142 is present beneath removable outer insulation 144. Continuous outer conductor layer 142 can be made of materials as previously discussed with respect to FIG. 4.

Though not shown, other embodiments of the outer conductor, such as a coil of conductive material one or more longitudinal ribbons of conductive materials, one or more spirally wound conductive ribbons, a continuously interwoven conductive mesh and a continuously interwoven mesh of dielectric materials embedded with a conductor are completely within the spirit and scope of the present invention.

Figure 11:
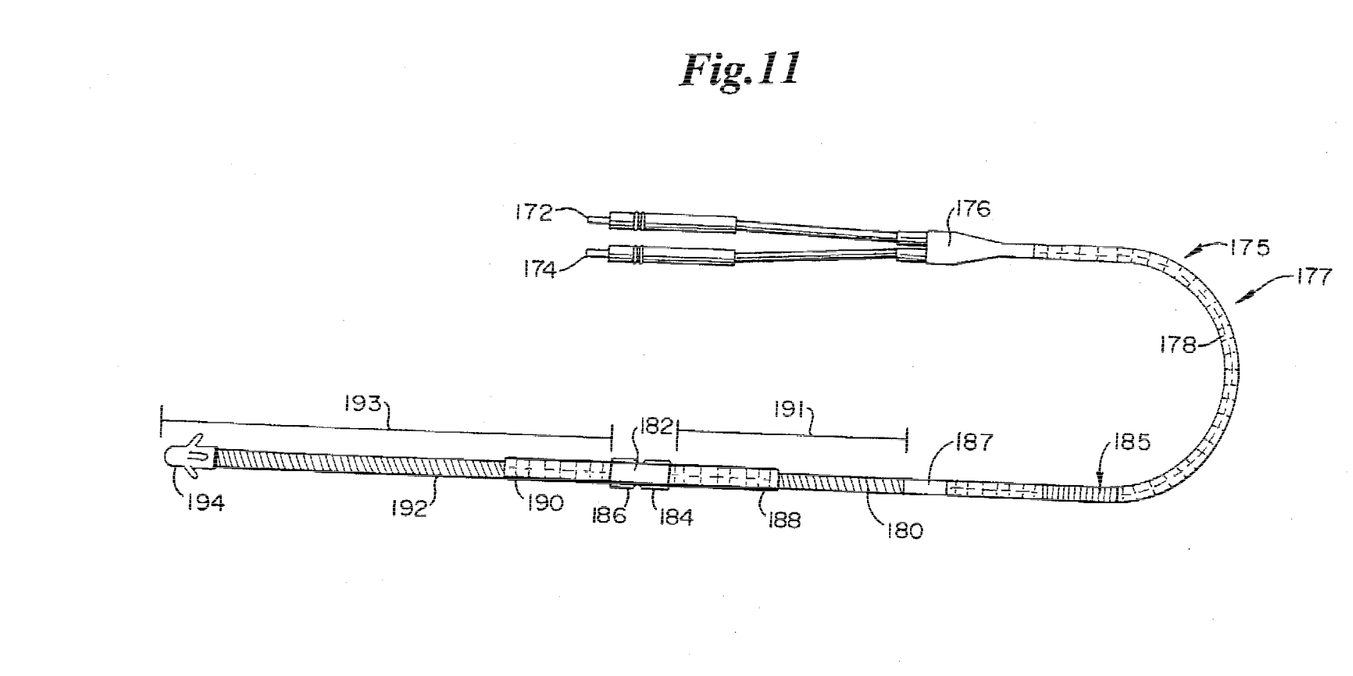
FIG. 11 depicts another embodiment of the present invention, wherein portions of ICD catheter lead electrodes are selectively exposed to create an optimum electrode length.

In FIG. 11 is depicted an alternate embodiment of the present invention within another catheter design, For other details of this embodiment, U.S. Pat. No. 5,454,839, assigned to the assignee of the present invention, is hereby incorporated by reference. In FIG. 11 is illustrated a plan view of visible members of a low profile defibrillation catheter 175. Catheter 175 includes junction member 176, electrical connectors 172 and 174, extending from junction member 176. Distal to junction member 176 is cable 177. Cable 177 has as its outer insulation, removable outer insulation 178. Removable outer insulation 178 is comprised of the same materials and is dividied into manually removable sections in the same manner as was discussed with respect to FIG. 4. Beneath removable outer insulation 178 is disposed an outer conductor 185. Outer conductor 185 preferably extends the length of cable 177 terminating distally at a junction with nonremovable outer insulation 187. Extending distally from nonremovable outer insulation 187 is proximal flexible wound electrode coil 180. Coil 180 extends distally, terminating within flared end 184. Flared end 184 is the proximal flared end of flexible plastic tubular covering 182. Flexible plastic tubular covering 182 has a distal flare 186, in which distal flexible wound electrode coil 192 terminates. Flexible wound electrode coil 192 originates within tined metal catheter tip 194 extending therefrom to within flared end 186. A distal portion of electrode coil 180 and a proximal portion of electrode coil 192 are enclosed in another removable outer insulation. Removable outer insulation 188 is the distal insulation covering coil 180. Removable outer insulation 190 encases the proximal portion of coil 192. Removable outer insulation segments 188 and 190 are divided into manually removable segments as earlier described with respect to FIGS. 4 and 9. These removable outer insulation segments further enable the effective length of electrode coils 180 and 192 to be adjusted by the implanting physician. Upon obtaining measurements, such as the distance from the right ventricular apex to the tricuspid valve and from the tricuspid valve to the junction of the right auricle and superior vena cava, the lengths of these electrodes can thereby be adjusted. The overall length of coil electrode 192 as represented by distance 193 is on the average about 8 centimeters. The overall length of electrode coil 180 is about 8 centimeters, as well. However, with patients having larger or smaller heart ventricles and auricles, electrode lengths of differing sizes may be necessary in order to enable the implanting physician to further adjust effective electrode length of electrode coils 192 and 180. While shown for the embodiment of FIG. 11, the removable outer insulation segments 188 and 190 could also be utilized with respect to the embodiments depicted in FIGS. 4, 5 and 6. Furthermore, removable outer insulative sections could also be present covering a proximal portion of electrode coil 180 and a distal portion of electrode 192 and still be within the spirit and scope of the present invention.

Because numerous modifications may be made of this invention without departing from the spirit thereof, the scope of the invention is not to be limited to the embodiments illustrated and described. Rather the scope of the invention is to be determined by appended claims and their equivalents.

What is claimed is:

1. A lead for delivering an electrical cardioversion/defibrillation countershock to a heart of a human patient comprising:

an elongated catheter body having a proximal end, a distal end and a catheter length, the catheter body including at least one electrical conductor and an outermost dielectric tubular sheath, at least one electrical conductor being electrically connected to an electrical connector located at the proximal end of the catheter body and to a cardioversion/defibrillation electrode located along the catheter body between the proximal end and the distal end, the cardioversion/defibrillation electrode having an exposed length;

at least a portion of the outermost dielectric tubular sheath including structure defining a removable portion of the outermost tubular sheath longitudinally adjacent the cardioversion/defibrillation electrode that is selectively separable and discardable from a remaining portion of the outermost tubular sheath, such that separation and removal of the removable portion creates an effective exposed length of the cardioversion/defibrillation electrode that is longer than the original exposed length.

2. The lead of claim 1, wherein the removable portion of the outermost tubular dielectric sheath is made from a substance selected from the group consisting of: silicone rubber, polytetrafluoroethylene resin, polyurethane, or any combination thereof.

3. The lead of claim 1, further comprising a second outermost tubular sheath, the second outermost tubular sheath disposed on an exterior of at least one of the cardiovesion/defibrillation electrodes, the second outermost tubular sheath including a structure defining a removable portion for selectively removing that portion of the outermost tubular sheath, thereby creating an effective exposed length of the cardioversion/defibrillation electrode that is longer than the original exposed length of that electrode.

4. The lead of claim 1, wherein the removable portion of the outermost tubular dielectric sheath is further comprised of a plurality of manually removable sections, thereby creating a selectable effective exposed length as subsequent ones of the sections are removed.

5. The lead of claim 4, wherein the removable portion of the outermost tubular dielectric sheath comprises perforations oriented generally longitudinally and circumferentially thereby defining the plurality of manually removable sections.

6. The lead of claim 4, wherein the removable portion of the outermost tubular dielectric sheath further comprises embedded filaments, the filaments extending generally longitudinally and circumferentially, thereby defining the plurality of manually removable sections.

7. An implantable system for delivering an electrical cardioversion/defibrillation countershock to the heart of a human patient, comprising:

an implantable pulse generator having a battery system, a capacitive charge storage system, a detection system and a control system for generating the electrical cardioversion/defibfillation countershock in response to a cardiac arrhythmia detected in the heart of the human patient;

an elongated catheter body having a proximal end, a distal end and a catheter length, the catheter body including at least one electrical conductor and an outermost dielectric tubular sheath, at least one electrical conductor being electrically connected to an electrical connector located at the proximal end of the catheter body and to a cardioversion/defibrillation electrode located along the catheter body between the proximal end and the distal end, the electrical connector being coupled to an electrical contact in the connector housing of the pulse generator; and at least a portion of the outermost dielectric tubular sheath including structure defining a removable portion of the outermost tubular sheath longitudinally adjacent the cardioversion/defibrillation electrode that is selectively separable and discardable from a remaining portion of the outermost tubular sheath, such that separation and removal of the removable portion creates an effective exposed length of the cardioversion/defibrillation electrode that is longer than an original exposed length of that electrode.

8. The implantable system of claim 7, further comprising a second outermost tubular sheath, the second outermost tubular sheath disposed on the exterior of at least one of the cardioversion/defibrillation electrodes, the second outermost tubular sheath including a structure defining a removable portion for selectively removing that portion of the outermost tubular sheath, thereby creating an effective exposed length of the cardioversion/defibrillation electrode that is longer than the original length of that electrode.

9. The implantable system of claim 7, wherein the removable portion of the outermost tubular dielectric sheath is made from a substance selected from the group consisting of: silicone rubber, polytetrafluoroethylene resin, polyurethane, or any combination thereof.

10. The implantable system of claim 7, wherein the removable portion of the outermost tubular dielectric sheath is further comprised of a plurality of manually removable sections, thereby creating a selectable effective exposed length as subsequent ones of the sections are removed.

11. The implantable system of claim 10, wherein the removable portion of the outermost tubular dielectric sheath comprises perforations oriented generally longitudinally and circumferentially thereby defining sections, the plurality of manually removable sections.

12. The implantable system of claim 10, wherein the removable portion of the outermost tubular dielectric sheath is further comprised embedded filaments, the filaments extending generally longitudinally and circumferentially, thereby defining the plurality of manually removable sections.

* * * * *